United States Patent
Jordan et al.

(10) Patent No.: US 9,814,701 B2
(45) Date of Patent: Nov. 14, 2017

(54) COMPOSITIONS AND METHODS FOR THE TREATMENT OF MACULAR DEGENERATION

(75) Inventors: Thomas A. Jordan, Lexington, MA (US); John Clifford Chabala, Scotch Plains, NJ (US); Gerald D. Cagle, Fort Worth, TX (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 944 days.

(21) Appl. No.: 13/514,769

(22) PCT Filed: Dec. 9, 2010

(86) PCT No.: PCT/US2010/059719
§ 371 (c)(1),
(2), (4) Date: Aug. 17, 2012

(87) PCT Pub. No.: WO2011/072141
PCT Pub. Date: Jun. 16, 2011

(65) Prior Publication Data
US 2012/0302601 A1    Nov. 29, 2012

Related U.S. Application Data

(60) Provisional application No. 61/285,745, filed on Dec. 11, 2009.

(51) Int. Cl.
*A61K 31/47*    (2006.01)
*A61K 47/40*    (2006.01)
*A61K 9/00*     (2006.01)
*A61K 31/423*   (2006.01)

(52) U.S. Cl.
CPC .......... *A61K 31/423* (2013.01); *A61K 9/0048* (2013.01); *A61K 31/47* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 2,086,186 A | 7/1937 | Messer | |
| 5,472,954 A | 12/1995 | Loftsson | |
| 5,493,027 A | 2/1996 | Nichols et al. | |
| 5,668,117 A | 9/1997 | Shapiro | |
| 6,191,127 B1 | 2/2001 | Holscher et al. | |
| 6,444,221 B1 | 9/2002 | Shapiro | |
| 6,498,154 B1 | 12/2002 | Grubb et al. | |
| 7,973,025 B2 | 7/2011 | Jordan et al. | |
| 7,982,071 B2 | 7/2011 | Scott | |
| 8,722,669 B2 | 5/2014 | Palczewski et al. | |
| 8,940,721 B2 | 1/2015 | Jordan | |
| 8,940,764 B2 | 1/2015 | Jordan | |
| 2004/0132636 A1 | 7/2004 | Dooley | |
| 2005/0020603 A1 | 1/2005 | Dai | |
| 2005/0090553 A1 | 4/2005 | Shapiro | |
| 2005/0130906 A1 | 6/2005 | Matier | |
| 2005/0197292 A1 | 9/2005 | Smithson et al. | |
| 2005/0234018 A1 | 10/2005 | Lyons et al. | |
| 2006/0014786 A1 | 1/2006 | Raut | |
| 2006/0111318 A1 | 5/2006 | Okamoto | |
| 2006/0183909 A1 | 8/2006 | Schmitt et al. | |
| 2006/0189608 A1 | 8/2006 | Bingaman | |
| 2007/0129404 A1 | 6/2007 | Hagihara et al. | |
| 2007/0135481 A1* | 6/2007 | Jordan et al. | 514/313 |
| 2012/0108585 A1 | 5/2012 | Vu | |
| 2012/0302601 A1 | 11/2012 | Jordan et al. | |
| 2014/0235604 A1 | 8/2014 | Palczewski et al. | |
| 2015/0209333 A1 | 7/2015 | Jordan | |
| 2015/0209345 A1 | 7/2015 | Jordan | |
| 2015/0335632 A1 | 11/2015 | Brady | |
| 2015/0344447 A1 | 12/2015 | Chabala | |

FOREIGN PATENT DOCUMENTS

| | | |
|---|---|---|
| EP | 0186367 A2 | 7/1986 |
| EP | 0245054 A1 | 11/1987 |
| EP | 0483881 A1 | 5/1992 |
| EP | 1621199 A1 | 1/2006 |
| EP | 2301549 A1 | 3/2011 |
| EP | 1888548 B1 | 8/2012 |
| JP | 2007/532648 A | 11/2007 |
| JP | 2008/542291 A | 11/2008 |

(Continued)

OTHER PUBLICATIONS

Ueda et al., Evaluation of a sulfobutyl ether beta-cyclodextrin as a solubilizing/stabilizing agent for several drugs, Drug Dev Ind Pharm. Sep. 1998;24(9):863-7, printed from http://www.ncbi.nlm.nih.gov/pubmed/9876538, abstract only, 1 page.*
FDA, BAM R59: Phosphate-Buffered Saline (PBS), pH 7.4, 2001, printed from http://www.fda.gov/Food/FoodScienceResearch/LaboratoryMethods/ucm062268.htm, 1 page.*
Del Valle, Cyclodextrins and their uses: a review, Process Biochemistry, vol. 39, Issue 9, May 31, 2004, pp. 1033-1046.*
Written Opinion of the International Searching Authority for PCT/US10/59719, dated Feb. 8, 2011.
Acland et al., "Gene Therapy Restores Vision in a Canine Model of Childhood Blindness," Nature Genetics, vol. 28, May 2001 (pp. 92-95).

(Continued)

*Primary Examiner* — Gigi Huang
(74) *Attorney, Agent, or Firm* — Andrea L. C. Reid; Dechert LLP

(57) ABSTRACT

The present invention is directed to topical ophthalmic compositions of a lipophilic compound and an oligomeric or polymeric carrier wherein the compositions are useful in the treatment and prevention of macular degeneration. The invention also includes methods of treating macular degeneration by using a topical ophthalmic composition of a lipophilic compound and an oligomeric or polymeric carrier.

10 Claims, 3 Drawing Sheets

(56) References Cited

FOREIGN PATENT DOCUMENTS

| WO | WO-9622992 A1 | 8/1996 |
|---|---|---|
| WO | WO-9805645 | 2/1998 |
| WO | WO-9946237 A1 | 9/1999 |
| WO | WO-01/41757 A1 | 6/2001 |
| WO | WO-2004082622 A2 | 9/2004 |
| WO | WO-2004/091630 A1 | 10/2004 |
| WO | WO-2005035506 A1 | 4/2005 |
| WO | WO-2005079774 A2 | 9/2005 |
| WO | WO-2005/105067 A2 | 11/2005 |
| WO | WO-2006002473 A1 | 1/2006 |
| WO | WO-2006049968 A1 | 5/2006 |
| WO | WO-2006/127945 A1 | 11/2006 |
| WO | WO-2007118276 A1 | 10/2007 |
| WO | WO-2008014602 A1 | 2/2008 |
| WO | WO-2010133672 A1 | 11/2010 |
| WO | WO-2011008202 A1 | 1/2011 |
| WO | WO-2011071995 A2 | 6/2011 |
| WO | WO-2012097173 A2 | 7/2012 |
| WO | WO-2012105887 A1 | 8/2012 |
| WO | WO-2014116593 A1 | 7/2014 |
| WO | WO-2014116836 A2 | 7/2014 |
| WO | WO-2015187942 A1 | 12/2015 |
| WO | WO-2016085939 A2 | 6/2016 |

OTHER PUBLICATIONS

Aldini et al., "Lipoxidation-Derived Reactive Carbonyl Species as Potential Drug Targets in Preventing Protein Carbonylation and Related Cellular Dysfunction," ChemMedChem, vol. 1, No. 10, Dec. 2006 (pp. 1045-1058).

Atkinson et al., "Triazaphenanthrenes. Part VI.* Further Observations on the Widman-Stoermer and Brosche Reactions," Journal of Chemical Society, pp. 2053-2060, 1966.

Bernstein et al., "Short-Circuiting the Visual Cycle with Retinotoxic Aromatic Amines," Proceedings of the National Academy of Sciences U.S.A., vol. 83, No. 6. Mar. 1, 1986 (pp. 1632-1635).

Bucciantini et al.. "Inherent Toxicity of Aggregates Implies a Common Mechanism for Protein Misfolding Diseases," Nature, vol. 416, No. 6880. Apr. 2002 (pp. 507-511).

Bureham et al., "Aldehyde-Sequestering Drugs: Tools for Studying Protein Damage by Lipid Peroxidation Products," Toxicology, vols. 181-182, Dec. 27, 2002 (pp. 229-236).

Chapple et al., "Unfolding Retinal Dystrophies: a Role for Molecular Chaperones?" Trends in Molecular Medicine, vol. 7, No. 9, Sep. 2001 (pp. 414-421).

ClinicalTrials.gov identifier NCT02578914, *A Safety and Activity Study of NS2 in Subjects with Allergic Conjunctions*, first received date Oct. 8, 2015; https://clinicaltrials.gov/ct2/show/NCT02578914.

Clinical Trials Results for Outcome Measures of Ocular Itching and Ocular Tearing (2016), NST achieved reductions in ocular itching and tearing that were clinically relevant and statistically greater than vehicle, 1 page.

Conover et al., "Thiazole Analogs of Pyridoxine," Journal of the American Chemical Society, vol. 72, No. 11, Nov. 1950 (pp. 5221-5225).

De Jong, "Age-Related Macular Degeneration," The New England Journal of Medicine, 355:1474-1485 (2006).

Dowling, "Neural and Photochemical Mechanisms of Visual Adaptation in the Rat," Journal of General Physiology, vol. 46, No. 6, Jul. 1963 (pp. 1287-1301).

Drysdale et al., "Complex Promoter and Coding Region $\beta_2$-adrenergic Receptor Haplotypes Alter Receptor Expression and Predict in vivo Responsiveness," Proceedings of the National Academy of Sciences U.S.A., vol. 97, No. 19, Sep. 2000 (pp. 10483-10488).

English Translation of: Westphal et al., "Reactions with Pryridinium Pyruvic Acid Esters," Pharmazie, vol. 31, No. 11, No Month Listed 1976 (pp. 770-773).

Fowler et al., "Coloured Complexes of all-*trans*-retinal with Benzocaine and Other Local Anesthetics," Journal of Photochemistry and Photobiology B: Biology, vol. 8, No. 2, Jan. 1991 (pp. 183-188).

Godard et al., "Sur les orthoamino formyl quinoléines, nouveaux synthons hétérocycliques," Journal of Heterocyclic Chemistry, 17(3):465-473, 1988.

Hubbard, "Geometrical Isomerization of Vitamin A, Retinene and Retinene Oxime," Journal of the American Chemical Society, vol. 78, No. 18, Sep. 1, 1956 (pp. 4662-4667).

Hurd et al., "Reaction of Propiolactone with Aniline Derivatives," Journal of the American Chemical Society, vol. 74, No. 23, Dec. 1952 (pp. 5889-5893).

International Preliminary Report on Patentability issued by the Korean Intellectual Property Office as International Searching Authority for International Application No. PCT/US2013/076592 dated Apr. 30, 2014 (6 pages).

International Preliminary Report on Patentability issued by the Korean Intellectual Property Office as International Searching Authority for International Application No. PCT/US2014/012356 dated May 30, 2014 (7 pages).

International Preliminary Report on Patentability issued by the United States Patent and Trademark Office as International Searching Authority for International Application No. PCT/US2014/012762 dated Jul. 18, 2014 (8 pages).

International Search Report and Written Opinion issued by the Korean Intellectual Property Office as International Searching Authority for International Application No. PCT/US2013/076592 dated Apr. 30, 2014 (10 pages).

International Search Report and Written Opinion issued by the Korean Intellectual Property Office as International Searching Authority for International Application No. PCT/US2014/012356 dated May 30, 2014 (11 pages).

International Search Report and Written Opinion issued by the United States Patent and Trademark Office as International Searching Authority for International Application No. PCT/US2014/012762 dated Jul. 18, 2014 (11 pages).

Ito et al., "A Medium-Term Rat Liver Bioassay for Rapid in vivo Detection of Carcinogenic Potential of Chemicals," Cancer Science, vol. 94, No. I, No Month Listed 2003 (pp. 3-8).

Karan et al., Lipofuscin Accumulation, Abnormal Electrophysiology, and Photoreceptor Degeneration in Mutant *ELOVL4* Transgenic Mice: A Model for Macular Degeneration, Proceedings of the National Academy of Sciences U.S.A., vol. 102, No. 11, Mar. 2005 (pp. 4164-4169).

Landor et al., "Allenes. Part 49, 4-Amino-2-(1-hydroxyalkyl)quinolones from Phenylhydroxylamine and Allenic Nitrites," Journal of the Chemical Society, Perkin Transactions 1, No. 2, No Month Listed 1989 (pp. 251-254).

Li et al., "Effect of Vitamin A Supplementation on Rhodopsin Mutants Threonine-17 → Methionine and Proline-347 → Serine in Transgenic Mice and in Cell Cultures," Proceedings of the National Academy of Sciences U.S.A., vol. 95, No. 20, Sep. 1998 (pp. 11933-11938).

Negre-Salvayre et al., "Advanced Lipid Peroxidation End Products in Oxidative Damage to Proteins. Potential Role in Diseases and Therapeutic Prospects for the Inhibitors," British Journal of Pharmacology, vol. 153, No. I, Jan. 2008 (pp. 6-20).

Nema et al., "Excipients and Their Use in injectable Products," PDA Journal of Pharmaceutical Science and Technology, vol. 51, No. 4, Jul.-Aug. 1997 (pp. 166-171).

Nerurkar et al., "β-Aryl-Glutaconic Acids, II. Imides of Certain β-aryl-Glutaconic and Glutaric Acids," Journal of Organic Chemistry, vol. 24, No. 12, Dec. 1959 (pp. 2055-2056).

Noorwez et al., "Pharmacological Chaperone-mediated in Vivo Folding and Stablization of the P23H-Opsin Mutant Associated with Autosomal Dominant Retinitis Pigmentosa," Journal of Biological Chemistry, vol. 278. Feb. 2003 (pp. 14442-14450).

Parish et al., "Isolation and One-Step Preparation of A2E and iso-A2E, Fluorophores from Human Retinal Pigment Epithelium," Proceedings of the National Academy of Sciences U.S.A., vol. 95, No. 5, Dec. 1998 (pp. 14609-14613).

(56) References Cited

OTHER PUBLICATIONS

Radu et al., "Treatment with Isotretinoin Inhibits Lipofuscin Accumulation in a Mouse Model of Recessive Stargardt's Macular Degeneration," Proceedings of the National Academy of Sciences U.S.A., vol. 100, No. 8, Apr. 2003 (pp. 4742-4747).

Rapp et al., "The Effects of Local Anaesthetics on Retinal Function," Vision Research, vol. 22, No. 9, No Month Listed 1982 (pp. 1087-1235).

Search Report and Written Opinion issued by the Intellectual Property Office of Singapore for Singapore Patent Application No. 11201505587Y dated Jul. 12, 2016 (12 pages).

Search Report and Written Opinion issued by the Intellectual Property Office of Singapore for Singapore Application No. 11201504859Y dated Aug. 1. 2016 (12 pages).

Sherman et al., "Cellular Defenses Against Unfolded Proteins: A Cell Biologist Thinks about Neurodegenerative Diseases," Neuron, vol. 29, No. I , Jan. 2001 (pp. 15-32).

Sieving et al., "Inhibition of the Visual Cycle in vivo by 13-cis Retinoic Acid Protects from Light Damage and Provides a Mechanism for Night Blindness in Isotretinoin Therapy," Proceedings of the National Academy of Sciences U.S.A., vol. 98. No. 4, Feb. 2001 (pp. 1835-1840).

Snell et al., "A novel structure having antagonist actions at both the glycine site of the N-Methyl-D-Aspartate receptor and neuronal voltage-sensitive sodium channels: Biochemical, electrophysiological, and behavioral characterization," Journal of Pharmacology and Experimental Therapeutics, vol. 292, No Month Listed 2000 (pp. 215-227).

Sparrow et al., "Phospholipid meets all-trans-retinal: the making of RPE bisretinoids," J. Lipid Res. 51(2):247-61 Epub Aug. 7, 2009.

Supplementary European Search Report issued by the European Patent Office for European Patent Application No. EP13865015.5 dated Mar. 31, 2016 (9 pages).

Supplementary Partial European Search Report issued by the European Patent Office for European Patent Application No. 14743711.5 dated Jul. 20, 2016 (14 pages).

Tian et al., "First total synthesis and determination of the absolute configuration of 1-N-methyl-3-methylamino-[N-butanoicacid-3-(9-methyl-8-propen-7-one)-amide]-benzo[f][1,7]naphthyridine-2-one, a novel benzonaphthyridine alkaloid," Tetrahedron Letters, 53:4892-4895, 2012.

Vlaskina et al., "Novel Synthesis of Substituted Benzimidazoles by Reduction of Esters of 4-Alkylamino-3,5-dinitrobenzoic Acids by Tin Chloride," Chemistry of Heterocyclic Compounds, vol. 4, No. 4, Apr. 2004 (pp. 523-524).

Voziyan et al., "A Post-Amadori Inhibitor Pyridoxamine also Inhibits Chemical Modification of Proteins by Scavenging Carbonyl Intermediates for Carbohydrate and Lipid Degradation," The Journal of Biological Chemistry, vol. 277, No. 5, Feb. 1, 2002 (pp. 3397-3403).

Wang et al., "A facile one-pot synthesis of 2-substituted-3-aminoquinolines: Preparation of benzo[b]naphthyridine-3-carbonitriles," Tetrahedron, vol. 60, No. 13, No Month Listed 2004 (pp. 2937-2942).

Weng et al., "Insights into the Function of Rim Protein in Photoreceptors and Etiology of Stargardt's Disease from the Phenotype in abcr Knockout Mice," Cell. vol. 98, No. 1, Jul. 1999 (pp. 13-23).

Westphal et al., "Reactions with Pryridinium Pyruvic Acid Esters," Pharmazie, vol. 31, No. 11, No Month Listed 1976 (pp. 770-773).

Wolkenberg et al., "Design, Synthesis, and Evaluation of Novel 3,6 Diaryl-4-aminoalkoxyquinolones as Selective Agonists of Somatostatin Receptor Subtype 2," J Med. Chem. 54:2351-2358 (2011).

Wood et al., "Aldehyde Load in Ischemia-Reperfusion Brain Injury: Neuroprotection by Neutralization of reactive Aldehydes with Phenelzine," Brain Research, vol. 1122, No. 1, Nov. 29, 2006 (pp. 184-190).

Zagol-Tkapitte et al., "Characterization of scavengers of γ-ketoaldehydes that do not inhibit prostaglandin biosynthesis." Chemical Research in Toxicology, vol. 23, No. 1, Jan. 2010 (pp. 240-250).

* cited by examiner

COMPOSITIONS AND METHODS FOR THE TREATMENT OF MACULAR DEGENERATION

CROSS-REFERENCE TO RELATED APPLICATIONS

This application is a National Stage of International Application No. PCT/US2010/059719, filed Dec. 9, 2010, which claims the benefit under 35 U.S.C. §119(e) of U.S. Provisional Application No. 61/285,745 filed Dec. 11, 2009, the entire contents of which is incorporated herein by reference.

BACKGROUND OF THE INVENTION

Macular degeneration is a leading cause of progressive blindness. The macula is the central region of the retina and contains the fovea where high acuity central vision is processed. Macular degeneration is a neurodegenerative disease in the macula that progressively causes disabling deficits in visual function.

There are multiple forms of macular degeneration. Age-related macular degeneration (AMD) is the most common form and first appears at middle age or later. In AMD patients, the dry form normally occurs first and develops with no vascular complications. Its clinical signs include an increase in fundus auto-fluorescence (FAF) and the formation of extracellular deposits called soft drusen, both caused by the accumulation of lipofuscin in retinal pigment epithelial (RPE) cells as discussed below. About 40% of dry AMD patients progress to an advanced form of the disease called geographic atrophy (GA) secondary to dry AMD, which is characterized by one or more atrophic retinal lesions caused by the localized death of RPE cells and adjacent retinal photoreceptor cells. Another 10% of dry AMD patients progress to wet AMD, which is characterized by neovascular growth from the choroid into the retina in response to VEGF signaling by RPE cells that are undergoing severe oxidative stress from A2E toxicities. Choroidal neovascular growth disrupts retinal tissue and destroys visual function in regions of the macula where this occurs. Finally, there is an early onset form of macular degeneration called Stargardt's disease which first appears in teenagers and young adults. Stargardt's disease is believed to have the same etiology as dry AMD.

Multiple lines of evidence indicate that macular degeneration is caused by the cytotoxic accumulation in RPE cells of naturally occurring bis-retinoid compounds including A2E (Sparrow J R, Wu Y, Kim C Y, Zhou J. Phospholipid meets all-trans-retinal: the making of RPE bisretinoids. J Lipid Res. 2009 Aug. 7 e-published). A2E is a reaction product of all-trans retinaldehyde (RAL) and phosphatidylethanolamine (PE), a membrane phospholipid found in the disc membranes of photoreceptor outer segments. The RAL that reacts with PE escapes from the visual cycle (step 3b in FIG. 1), a metabolic pathway in the back of the eye that (i) converts vitamin A from an alcohol (retinol) to a photo-reactive aldehyde (11-cis-retinaldehyde) for use in photo-transduction by opsin proteins in photoreceptor cell outer segments, and (ii) converts RAL to retinol after photo-transduction. As RAL escapes the visual cycle, A2E precursors form reversibly in photoreceptor outer segments, which are ingested by neighboring RPE cells after diurnal shedding. The final and irreversible step in the biosynthesis of A2E takes place in the acidic environment of RPE cell lysosomes. As A2E accumulates in RPE cells, it gradually poisons them by multiple cytotoxic mechanisms including lysosomal failure. This leads to the accumulation of undigested cellular debris called lipofuscin, which contains A2E and can be detected clinically by FAF. As RPE cells deteriorate, they lose their ability to participate in the visual cycle and are unable to provide photoreceptors with other metabolic support required for normal retinal function (see FIG. 1; Lamb T D, Pugh E N, Dark adaptation and the retinoid cycle of vision. Prog. Retinal and Eye Res. 2004; 23:307). As their metabolic support is withdrawn, photoreceptors fail to renew their shed outer segments and visual function is progressively lost. Reducing A2E formation will allow RPE cells to recover from A2E poisoning and resume their normal metabolic support of photoreceptor cells.

WO 2006/127945 discloses compounds and compositions that have been shown to reduce the formation of A2E, which as described above is the underlying etiology of macular degeneration including dry AMD and Stargardt's disease. These compounds are designed to inhibit A2E biosynthesis by reducing the amount of free RAL available for reaction with PE in photoreceptor outer segments, which is the first step in the A2E biosynthetic pathway. These compounds are lipophilic by design (i.e. the logarithm of their measured or calculated partition constant between water and n-octanol [log P or c log P which are called log D or c log D respectively at pH 7.4 as used herein] is greater than 0), because their covalent reactions with RAL take place in the disc membranes of photoreceptor outer segments where A2E precursors form.

A different way to reduce A2E biosynthesis is to inhibit one or more proteins of the visual cycle, because when the visual cycle is inhibited, less RAL escapes the visual cycle and becomes available to react with PE and form A2E precursors. Chronic treatment with a visual cycle inhibitor has been shown to reduce A2E synthesis in mouse (Radu et al., Treatment with isotretinoin inhibits lipofuscin accumulation in a mouse model of recessive Stargardt's macular degeneration. Proc Natl Acad Sci USA. 2003; 100:4742). The clinical value of this treatment approach is limited by the fact that visual cycle inhibitors cause night blindness by lowering rod photoreceptor sensitivity, impair dark adaptation by slowing the dark adaptation rate, and cause retinoid toxicities by activating retinoic acid receptors (RAR) if the visual cycle inhibitor compound is a member of the retinoid class. Visual cycle inhibitors now in clinical development include fenretinide which is a retinoid compound, and ACU-4429 which reportedly is not a retinoid.

Other approaches to treating macular degeneration are based on neuroprotection mechanisms of action including but not limited to neurotrophic receptor agonists, anti-inflammatory compounds including complement cascade inhibitors, anti-apoptosis compounds, steroids and anti-oxidant compounds, and limiting the progression to wet AMD with VEGF receptor blockers which mitigate the effects of VEGF signaling by RPE cells that are in severe oxidative stress as a consequence of A2E toxicities.

SUMMARY OF THE INVENTION

In therapeutic and prophylactic use, topical ocular administration minimizes systemic exposure compared to oral dosing. The present invention provides formulations and methods for topical ocular dosing of lipophilic compounds which treat macular degeneration (including dry AMD, GA secondary to dry AMD, wet AMD and Stargardt's disease) by reducing the formation of A2E and other naturally occurring bis-retinoids, by reacting covalently with free RAL that escapes the visual cycle and would otherwise form precursors of these compounds. The lipophilic compounds within the scope of this invention are further defined by having a log P or c log P (log D or c log D at pH=7.4) greater than 0.

DETAILED DESCRIPTION OF THE INVENTION

Figure 1:
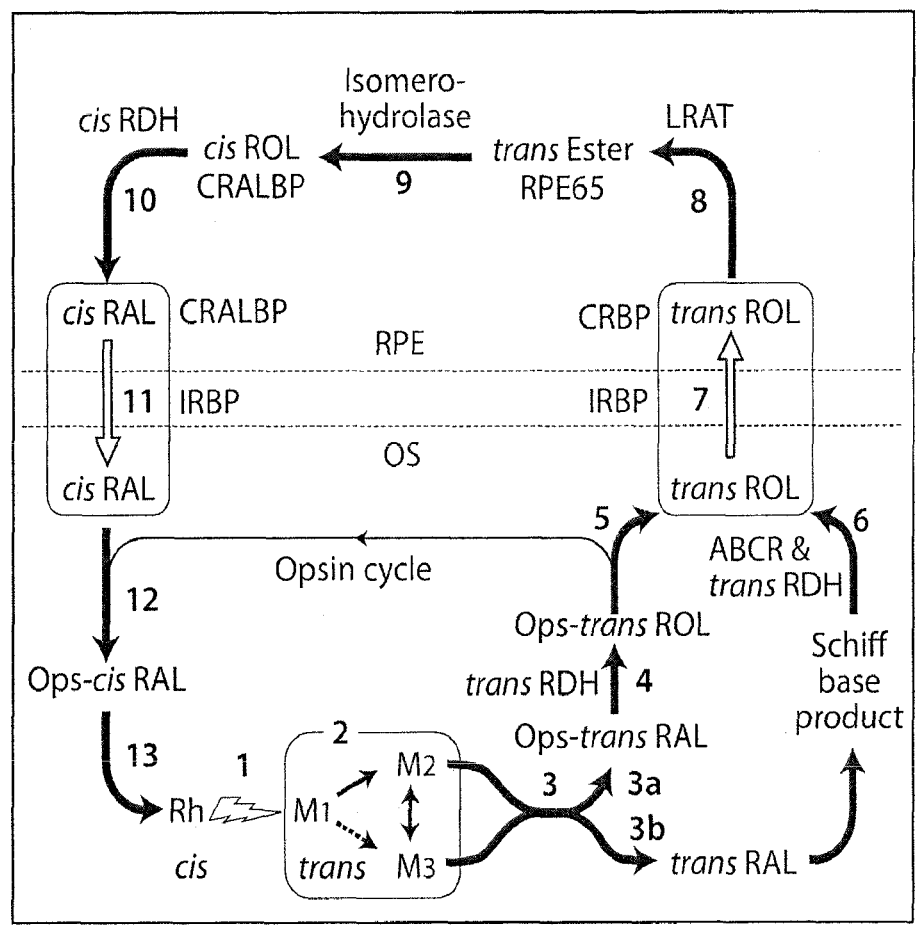
FIG. 1 depicts the visual cycle.

One embodiment of the present invention provides pharmaceutical compositions for treating macular degeneration (including dry AMD, GA secondary to dry AMD, wet AMD and Stargardt's disease). The root cause of macular degeneration is the cytotoxic accumulation in RPE cells of naturally occurring bis-retinoids including A2E. This accumulation can be lowered pharmacologically by limiting the amount of free RAL that escapes the visual cycle and otherwise reacts with PE to form their precursors. As the accumulation of these compounds is reduced pharmacologically, RPE cells can recover from cytotoxic damage and resume their metabolic support of photoreceptors which is essential for normal visual function. In publication WO 2006/127945, compounds are described which reduce A2E accumulation in this manner and are therefore useful in treating macular degeneration. The instant application incorporates by reference the subject matter of WO 2006/127945.

Lipophilic compounds which reduce A2E and thereby treat macular degeneration including dry AMD and Stargardt's disease by other means (e.g. by inhibiting the visual cycle) are also included within the scope of this invention. Such compounds include ACU-4429. All such compounds have a log P or c log P greater than 0.

In therapeutic or prophylactic use, topical ocular administration minimizes systemic exposure compared to oral dosing. However, most topical formulations have failed to deliver efficacious levels of drug to the retina which is the site of the mechanism of action. Surprisingly, applicants have found that by employing preparations containing a lipophilic active agent and a cyclodextrin, or chemically modified cyclodextrin including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium salt (or potassium salt), efficacious levels of the lipophilic active agent are delivered to the back of the eye and specifically to the RPE and retina. Pharmaceutical compositions of a lipophilic active agent and an oligomeric or a polymeric carrier such as a cyclodextrin or chemically modified cyclodextrin including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium salt (or potassium salt) are useful for the treatment of macular degeneration (including dry age-related macular degeneration, GA secondary to dry AMD, wet AMD and Stargardt's disease).

One exemplification of the present invention is represented by a topical ophthalmic composition containing an active lipophilic compound and an oligomeric or a polymeric carrier such as a cyclodextrin, or a chemically modified cyclodextrin including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium salt (or potassium salt) in an aqueous solution or a gel dispersion. Such active lipophilic compounds include those that reduce A2E by reacting covalently with RAL, e.g. the compounds of WO 2006/127945. Illustrative of such compounds are those described in WO 2006/127945 the contents of which application are herein incorporated by reference. Exemplifying the compounds which may be employed in the instant invention are the compounds of formula Ia:

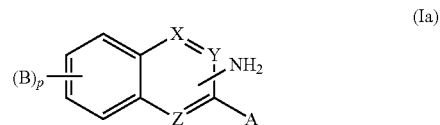

(Ia)

and pharmaceutically acceptable salts thereof, wherein X, Y, and Z are each, independently, N, CH, C with the NH$_2$ attached, or absent, such that one of X, Y, and Z is N; p is 0, 1, 2, or 3, B is a halogen atom, hydroxyl, carbamoyl, amino, or aryl, A is

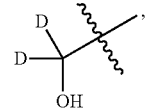

D is unbranched lower alkyl. Specifically, compound A of paragraph (00027) of WO 2006/127945 and pharmaceutically acceptable salts thereof may be employed in the instant invention.

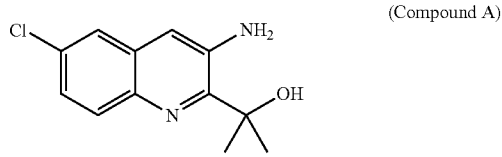 [SMILES: CC(C)(O)c1nc2ccc(Cl)cc2cc1N]

(Compound A)

Further illustrating the useful compounds herein are the compounds of formula IIIa:

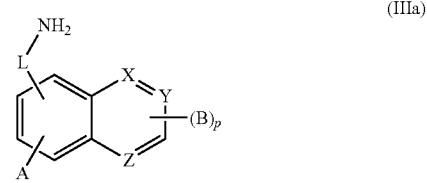

(IIIa)

and pharmaceutically acceptable salts thereof, wherein L is a single bond or CH$_2$; X, Y, and Z are each, independently, N, NH, O, S, CB, CH, or absent, such that one of X, Y, and Z is N or NH; p is 0, 1, 2, or 3; B is a halogen atom, hydroxyl, carbamoyl, aryl or amino; A is

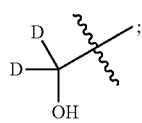

and D is unbranched lower alkyl; and

Specifically, compounds B and C of paragraph (00046) of WO 2006/127945, and pharmaceutically acceptable salts thereof may be employed in the instant invention.

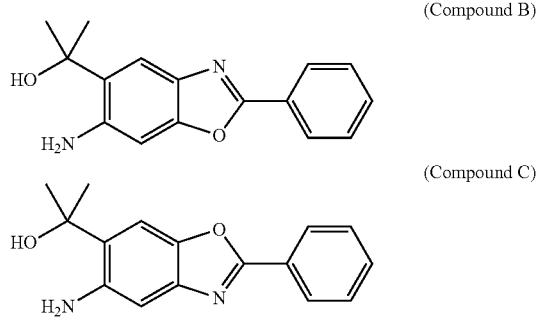

The amount of active agent in the composition will vary dependent on the intrinsic activity of the compound. However, for compounds of formula Ia and formula IIIc the amount will generally be from 0.01-1.0% weight/volume and more particularly 0.1% to 0.5% weight/volume. In each case a compound as described above may be used or a pharmaceutically acceptable salt of said compound. The term lipophilic compound is meant to include the compound and its pharmaceutically acceptable salts. A pharmaceutically acceptable salt herein means a salt that is capable of being topically delivered to the eye of a patient. The carrier in the composition is an oligomeric or a polymeric carrier such as a cyclodextrin including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium salt (or potassium salt). Exemplifying an oligomeric or a polymeric carrier is β-cyclodextrin sulfobutylether sodium salt. The amount of β-cyclodextrin sulfobutylether sodium salt in the aqueous preparation may range from about 0.01% to 30% weight/volume. In one illustration the concentration of β-cyclodextrin sulfobutylether sodium salt is 5-25% weight/volume. Further illustrating the concentration of β-cyclodextrin sulfobutylether sodium salt is 9.5-20% weight/volume. In one exemplification the concentration of β-cyclodextrin sulfobutylether is 9.5% weight/volume.

It should be noted that, although the compositions are further illustrated with β-cyclodextrin sulfobutylether, each lipophilic agent may be formulated with each of the excipients. The composition may contain saline and be buffered with for example a phosphate buffer so that the pH of the composition is brought to a pH range of 5.5-8.5 or more particularly a pH of 6.5-7.5. A preservative may optionally be included in the composition. Such preservatives can include both chemical stabilizers and antiseptics. Compounds such as Compounds A are stable under the conditions of use, however other compounds may require the use of other excipients such as anti-oxidants.

A second embodiment of the invention is directed to a method of treating macular degeneration (including dry age-related macular degeneration, GA secondary to dry AMD, wet AMD and Stargardt's disease), by administering a topical formulation of an active lipophilic compound and a carrier to the eye(s) of a patient. In another embodiment, the present invention provides a topical ophthalmic composition for use in treating macular degeneration wherein said composition comprises an active lipophilic compound and a carrier or a pharmaceutically acceptable salt thereof in an aqueous solution. Exemplifying the carrier is β-cyclodextrin sulfobutylether or a pharmaceutically acceptable sat thereof. The active lipophilic compound in each of these embodiments includes those that reduce A2E by reacting with RAL, e.g. the compounds of WO 2006/127945. Examples of such compounds are those described in WO 2006/127945. Exemplifying such compounds are Compounds A, B and C. Lipophilic Compounds which function by other mechanisms such as ACU-4429 are also included. The term lipophilic compound is meant to include both the compound and its pharmaceutically acceptable salts. The excipient in the formulation is oligomeric or polymeric such as a cyclodextrin or a chemically modified cyclodextrin, more particularly including β-cyclodextrin sulfobutylether sodium salt (or potassium salt). It should be noted that, although particularly illustrated with β-cyclodextrin sulfobutylether, the method may be practiced with each lipophilic compound formulated with each excipient. The formulation may be buffered to a pH range of 5.5-8.5 or more particularly a pH of 6.5-7.5. The buffer may be a phosphate buffer. The formulation may be applied as an aqueous solution or a gel dispersion and the solution may be a saline solution. The accumulation of lipofuscin occurs in RPE cells in the back of the eye. Applicants have determined experimentally in animals that the use of topical compositions as described herein deliver pharmacologically active levels of lipophilic active drug safely to the back of the eye after topical ocular administration and are therefore useful in the treatment of macular degeneration (including dry age-related macular degeneration, GA secondary to dry AMD, wet AMD and Stargardt's disease). Efficacious levels are defined as those that reduce A2E accumulation significantly in animal studies.

Preparation of Compositions of the Invention

Formulations of a lipophilic active agent and an oligomeric or a polymeric carrier are prepared by stirring an aqueous suspension or solution of a polymeric carrier such as a cyclodextrin, or chemically modified cyclodextrin including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium (or potassium) salt with water, saline or phosphate-buffered saline at a temperature from 20° C. to 50° C., but preferably at ambient temperature, for 0.1-24 hr, depending on the polymeric carrier. The lipophilic active agent is added as a solid or neat liquid to the thus formed aqueous suspension or solution of polymeric carrier, and the resulting mixture is stirred at a temperature from 20° C. to 50° C., but preferably at ambient temperature, for 0.1-24 hr, but typically from 0.5-2 hr, depending on the lipophilic active agent. The thus formed formulation of a lipophilic active agent and an oligomeric or a polymeric carrier may then be treated with an aqueous solution of an inorganic or organic acid or an inorganic or organic base to adjust the pH of the solution as desired. To the formulation may also be added preservatives, including both chemical stabilizers and antiseptics.

Example 1—Preparation of a 0.1% w/v Aqueous Formulation of Compound A with 9.5% w/v β-Cyclodextrin Sulfobutylether The preparation was carried out in a 1000 ml beaker equipped with a stirring bar for mixing. Approximately 60% of the targeted weight of sterile water was added to the beaker. Stirring was adjusted so as not to incorporate air. Anhydrous dibasic sodium phosphate (0.83% of the total batch weight) and sodium phosphate monobasic monohydrate (0.017% of the total batch weight) was added to the vessel and mixed until dissolved. β-cyclodextrin sulfobutylether (9.5% of the total batch weight) was slowly added to the beaker and the solution mixed until dissolved. Compound A (0.1% of the total batch weight) was slowly added and mixed until dissolved. A sample was extracted and the pH measured. If the pH was not in the range 7.3±0.05, adjustment was made with 1N aqueous NaOH or 1N aqueous HCl. The batch weight was measured and the amount of sterile water needed to bring to final batch weight was determined and added.

Results of Applying Formulations to the Eyes of Mice and Rabbits.

1) Measurement of Levels of $^{14}$C-Compound A in the Posterior Eyecup of Mice.

The target tissue, for the biological activity of compounds which reversibly react with RAL, e.g. Compounds A, B and C, is the outer segment of retinal photoreceptor cells. To demonstrate that topical optical (TO) administration of Compound A delivers therapeutically useful amounts of, for example, Compound A to the retina, C57BL/6 mice, the parent strain of abcr −/− mice (knockout mouse), were treated intraperitoneally (IP) with $^{14}$C-Compound A at 10 mg/kg ("efficacious dose"), specifically a dose that when repeated daily for 56 days reduced A2E formation by 71% (p<0.01) in the abcr −/− mouse. At certain timepoints after topical ocular dosing, the eyes of the mice were enucleated and the posterior eyecup was dissected, extracted and analyzed by liquid scintillation chromatography (LSC) for $^{14}$C-Compound A. Thirty minutes after IP treatment with $^{14}$C-Compound A, the $C_{max}$ amount of $^{14}$C-Compound A in the posterior eyecup (i.e. the peak concentration at time $T_{max}$) was 14.36 μg/g. Fifteen minutes after TO treatment with a single 5 μL eyedrop containing 25 μg (0.5% weight/volume) $^{14}$C-Compound A in a composition containing 20% weight/volume β-cyclodextrin sulfobutylether sodium salt in phosphate-buffered saline, the equivalent amount of $^{14}$C-Compound A in the posterior eyecup was 13.12 μg/g, which is 90% of the $C_{max}$ value measured in the same ocular tissue after systemic treatment at an efficacious dose.

2) Ocular Levels of $^{14}$C-Compound A in the Retina and RPE of Rabbits.

Dutch belted rabbits were dosed TO with a single 40 μL eyedrop containing either 0.50%, 0.15% or 0.05% weight/volume $^{14}$C-Compound A in 20%, 6% or 2% weight/volume, respectively, β-cyclodextrin sulfobutylether sodium salt in phosphate-buffered saline (Table 1). At different times after dosing the eyes of the rabbits were enucleated, dissected and the amount of $^{14}$C-Compound A in the retina and RPE together was measured by LSC. Each value represents the mean value from 6 eyes. Significant amounts of $^{14}$C-Compound A were found in rabbit retina/RPE within one hour of TO dosing as shown in Table 1.

3) Topical Ocular Dosing with $^{14}$C-Compound A in Cynomolgus Macaques.

The pharmacokinetics (PK) of Compound A in four intraocular regions of Cynomolgus Macaques was measured after topical dosing of 40 μL per eye of 0.50% weight/volume $^{14}$C-Compound A in β-cyclodextrin sulfobutylether sodium salt in phosphate-buffered saline. Sampling of intraocular regions (vitreous humor, retina+RPE, anterior eyecup, and posterior eyecup) and blood for PK evaluation was conducted at 0.25, 0.5, 1, 3, 6 and 9 hours post dose.

Figure 2:
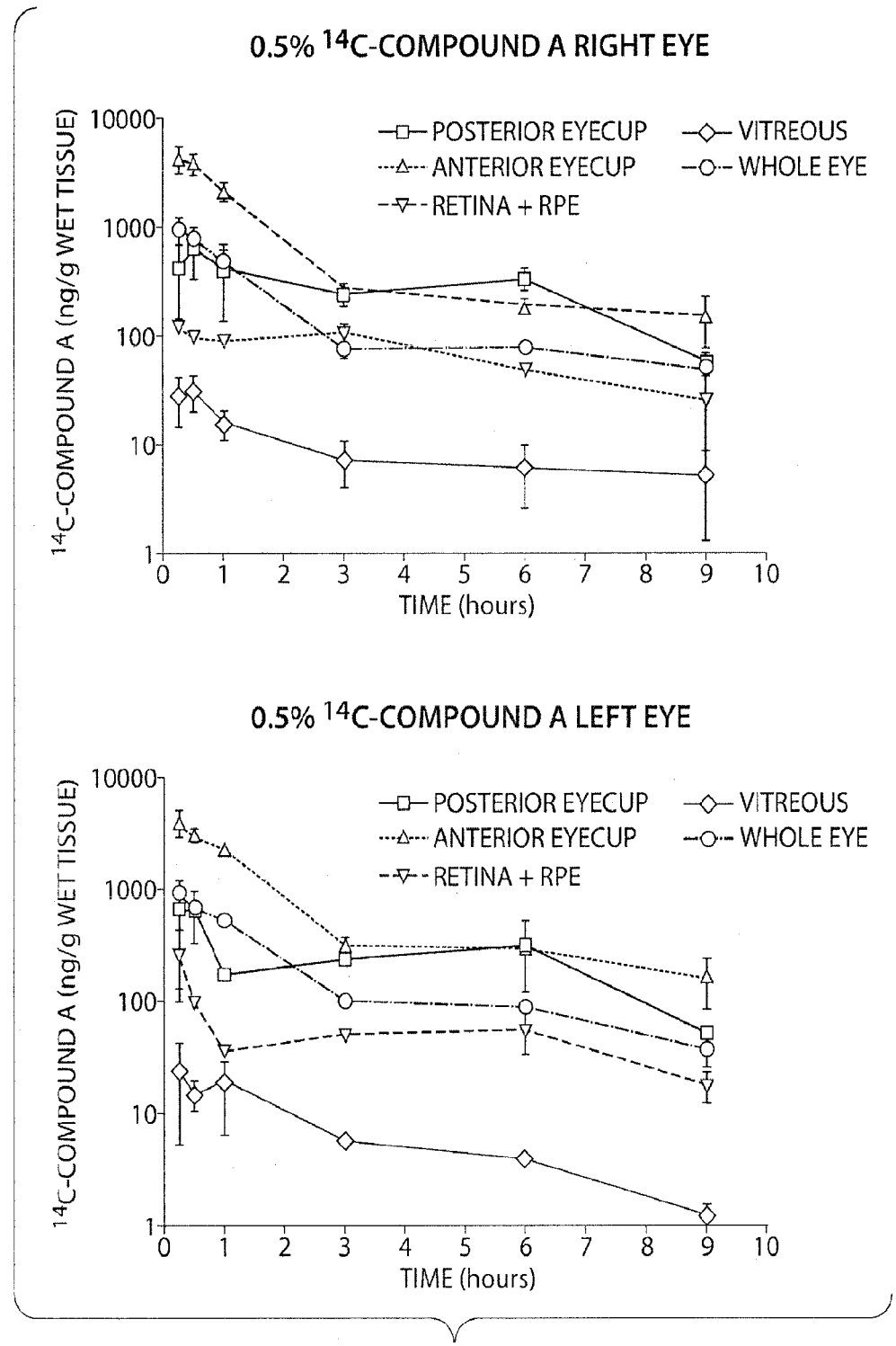
FIG. 2 depicts a time profile of the concentration of $^{14}$C-Compound A in ng/g of ocular tissue.

FIG. 2 shows the time course of $^{14}$C-Compound A concentration expressed in nanograms (ng) per gram (g) of ocular tissue.

TABLE 1

$^{14}$C-Compound A levels in rabbit retina and RPE after acute TO dosing in β-cyclodextrin sulfobutylether sodium salt.

| Compound A concentration in eyedrop (% w/v) | Amount applied of $^{14}$C-Compound A (ng) | βCSSA[1] (% w/v) | Amount of $^{14}$C-Compound A in retina and RPE at $t_{max}$ (ng/g) |
| --- | --- | --- | --- |
| 0.50% | 200 | 20% | 131 |
| 0.15% | 60 | 6% | 47.0 |
| 0.05% | 20 | 2% | 23.1 |

[1]β-cyclodextrin sulfobutylether sodium salt;
w/v = weight/volume.

4) Functional Biological Activity in Mice.

The biological activity in the retina of some drugs within the scope of the invention such as Compounds A, B and C cannot be measured non-invasively after topical ocular application because these drugs, e.g. Compounds A, B and C, do not alter the normal function of the retina. For example Compound A does not inhibit the visual cycle nor does it slow the rate of dark adaptation (DA), changes which can be measured by electroretinography (ERG) within minutes after equivalent treatment with a visual cycle inhibitor. The protocol for measuring DA rates by ERG is based on the kinetics of functional visual recovery from photo-bleaching of visual pigment by brief exposure to extremely bright light. Like Compounds A, B and C, retinoids are lipophilic compounds as defined above. As such, retinoids can be used to demonstrate that a small lipophilic compound in a composition containing β-cyclodextrin sulfobutylether sodium salt exhibits biological activity in the retina minutes to hours after topical application to the front of the eye.

Figure 3:
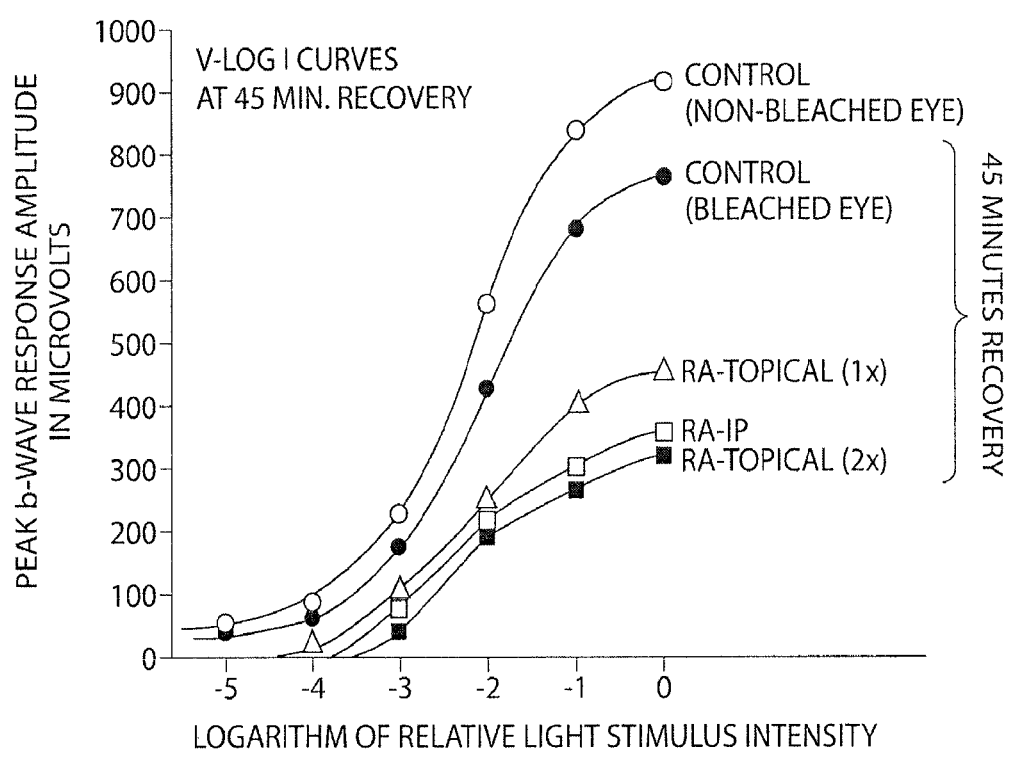
FIG. 3 depicts effects of RA treatment on dark adaptation rate in the mouse after acute TO or IP administration of 13-cis-retinoic acid.

A retinoid useful for this purpose is 13-cis-retinoic acid (RA, also known as isotretinoin). Mice treated IP at 20 mg/kg with RA show visual cycle inhibition (FIG. 3). Independent studies demonstrate that the visual cycle inhibition decreases A2E synthesis (Radu R A, Mata N L, Nusinowitz S, Liu X, Sieving P A, Travis G H. Treatment with isotretinoin inhibits lipofuscin accumulation in a mouse model of recessive Stargardt's macular degeneration. Proc Natl Acad Sci 2003; 100:4742). However, mice treated TO with one or two 30 μL eyedrops of a composition containing 0.2% weight/volume RA and 20% weight/volume β-cyclodextrin sulfobutylether sodium salt in phosphate-buffered saline showed a dose-responsive inhibition of DA similar to that observed after IP dosing (FIG. 3).

What is claimed is:
1. An ophthalmic composition comprising a compound of the following formula:

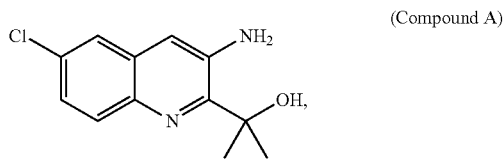 [SMILES: CC(C)(O)c1nc2ccc(Cl)cc2cc1N]

(Compound A)

or a pharmaceutically acceptable salt thereof;
β-cyclodextrin sulfobutylether or a pharmaceutically acceptable salt thereof; and an ophthalmically acceptable excipient;
wherein the compound is present at a concentration of about 0.05% w/v and wherein the ophthalmic composition comprises an aqueous solution.

2. The composition of claim 1, wherein the β-cyclodextrin sulfobutylether is the sodium salt of β-cyclodextrin sulfobutylether.

3. The composition of claim 1, wherein the aqueous solution is at a pH of 6.5-7.5.

4. The composition of claim 1, wherein the β-cyclodextrin sulfobutylether or pharmaceutically acceptable salt thereof is at a concentration of about 9.5-20% w/v.

5. The composition of claim 1, wherein β-cyclodextrin sulfobutylether or pharmaceutically acceptable salt thereof is at a concentration of about 9.5% w/v.

6. The composition of claim 1, wherein the β-cyclodextrin sulfobutylether or pharmaceutically acceptable salt thereof is at a concentration of about 0.01-30% w/v.

7. The composition of claim 1, wherein the β-cyclodextrin sulfobutylether or pharmaceutically acceptable salt thereof is at about 5-25% w/v.

8. The composition of claim 1, wherein the β-cyclodextrin sulfobutylether or pharmaceutically acceptable salt thereof is at about 2% w/v.

9. The composition of claim 1, wherein the ophthalmically acceptable excipient comprises a buffer.

10. The composition of claim 9, wherein the buffer comprises a phosphate buffer.

* * * * *